United States Patent [19]
Crispino et al.

[11] Patent Number: 6,136,972
[45] Date of Patent: Oct. 24, 2000

[54] PREPARATION OF A MANNICH BASE INTERMEDIATE FOR 2-[(4-HETEROCYCLIC-PHENOXYMETHYL)-PHENOXY]-ALKANOATES

[75] Inventors: Gerard A. Crispino, Princeton; Mark R. Diener, Pittstown, both of N.J.

[73] Assignee: FMC Corporation, Philadelphia, Pa.

[21] Appl. No.: 09/510,415

[22] Filed: Feb. 22, 2000

Related U.S. Application Data

[62] Division of application No. 09/212,216, Dec. 16, 1998.
[60] Provisional application No. 60/069,674, Dec. 12, 1997.

[51] Int. Cl.[7] ..................... C07D 265/30; C07C 229/00; C07C 215/00
[52] U.S. Cl. ..................... 544/174; 544/173; 544/106; 544/170; 560/42; 564/390
[58] Field of Search ............................... 560/42; 564/390; 544/173, 174

[56] References Cited

U.S. PATENT DOCUMENTS

| | | | |
|---|---|---|---|
| 4,214,094 | 7/1980 | Kamiya et al. | 560/42 |
| 4,217,235 | 8/1980 | Karlsson | 252/184 |
| 4,980,505 | 12/1990 | Pan et al. | 564/414 |

OTHER PUBLICATIONS

"Selective Synthesis of Phenolic Mannich Base Under Solid–Liquid Phase Transfer Conditions", 1st. Chim, Org., Univ. Parma, Parma, I–43 100, Italy Synthesis (1983), (11), 906–7 (CA 101:6729, 1984).

"1–Aryloxy–3–Substituted–Aminopropan–2–ols, Aminomethyl Substituted Phenols and 1,3–Benzoxazines as Potential Spermicides", Cent. Drug Res. Inst., Lucknow, 226 001, India, Indian J. Chem., Sect. B (1991), 30B(2), 281–5 (CA 114:185410, 1991).

"Synthesis of 2–Aminomethyl–5–Butylphenols", Faculty of Engineering, Toa University, Ichinomiya Gakuen–cho, Shimonoseki–shi, Yamaguchi, 750, Japan, Kyushu Daigaku Kino Busshitzu Kagaku Kenkyusho Hokoko (1997), 11(2), 125–129 (CA 130:168047, 1999).

*Primary Examiner*—Laura L. Stockton
*Attorney, Agent, or Firm*—FMC Corporation

[57] ABSTRACT

A Mannich base intermediate for 2-[(4-heterocyclic-phenoxymethyl)-phenoxyl]-alkanoates and methods for its preparation are provided. A method for preparation of an alkyl 2-[2-(secondary amino methyl)-5-alkylphenoxy]-alkanoate comprises the steps of: reacting a mixture of m-alkyl phenol, a secondary amine, and an aldehyde, with or without a catalyst, in a first solvent at reflux temperatures to form a 2-[(secondary amino)methyl]-5-alkylphenol. That product is then reacted with an alkyl 2-haloalkanoate, and an alkali metal carbonate, with or without a second catalyst in a second solvent at reflux temperatures to form the 2-[2-(secondary amino methyl)-5-alkylphenoxy]-alkanoate. The aldehyde may be paraformaldehyde, aqueous formaldehyde, formaldehyde, or polymerized acetal derivatives thereof. The first solvent may be acetonitrile or toluene. The catalyst may be an acid catalyst or a base catalyst. In the preferred embodiment the Mannich base is a 2-[(secondary amino)-methyl]-5-alkylphenol, or a 2-[2-(secondary amino methyl)-5-alkylphenoxy]-alkanoate.

15 Claims, No Drawings

PREPARATION OF A MANNICH BASE INTERMEDIATE FOR 2-[(4-HETEROCYCLIC-PHENOXYMETHYL)-PHENOXY]-ALKANOATES

This application is a division of Ser. No. 09/212,216 filed Dec. 16, 1998, which claims benefit of Ser. No. 60/069,674 filed Dec. 12, 1997.

This invention relates to a method for making Mannich base intermediates. More particularly, this invention relates to the preparation of intermediates that can be used to prepare herbicidal 2-[(4-heterocyclic-substituted-3-halophenoxymethyl)-phenoxy]-alkanoates. Still more particularly this invention relates to the preparation of phenol and alkanoate intermediates which can be converted into herbicidal 2-[(4-heterocyclic-substituted-3-halophenoxymethyl)-phenoxy]alkanoates.

Herbicidal 2-[(4-heterocyclic-subsituted-3-halophenoxymethyl)-phenoxy]-alkanoates and their method of manufacture have been disclosed in U.S. Pat. No. 5,344,812. The '812 patent discloses that an appropriately substituted methyl 2-(chloromethylphenoxy)alkanoate and an appropriately substituted 4-heterocyclic-substituted phenol are heated in N,N-dimethylformamide at 80° C. in the presence of at least a molar equivalent of potassium carbonate to form the herbicidal compound. This patent further discloses that the methyl 2-(chloromethyl-phenoxy) alkanoate intermediate is formed in a three step process illustrated in the disclosed "Schema A" process (column 4, line 26 et seq.). In particular, Example 1 discloses in Steps F and G that a 4-methylsalicylaldehyde is reacted with potassium carbonate and methyl 2-bromopropanoate to form methyl 2-(formyl-5-methylphenoxy)-propanoate. This propanoate is then reacted with sodium methoxide and sodium borohydride in the presence of methanol to form methyl 2-(2-hydroxymethyl-5-methylphenoxy)propanoate which in turn is reacted with thionyl chloride and pyridine in the presence of methylene chloride to form the methyl 2-(2-chloro-methyl-5-methylphenoxy)propanoate intermediate.

The Mannich reaction is described by F. F. Blicke in chapter 10 of Organic Reactions, Volume 1 (1942). Blicke discloses that the Mannich reaction consists in the condensation of ammonia or a primary or secondary amine, usually as the hydrochloride, with formaldehyde and a compound containing at least one hydrogen atom of pronounced reactivity. The essential feature of the reaction is the replacement of the active hydrogen atom by an aminomethyl or substituted aminomethyl group. The use of secondary amines in this reaction with ketones, aldehydes, acids, esters, phenols, acetylenes, picolines and quinaldines are described. In particular, Blicke discloses that the o- and p-hydrogens in phenols are sufficiently active to enter into the Mannich reaction; and that products have been reported resulting from phenol; 4-acteaminophenol; o- and p-cresol; m-cresol; 3,5-dimethylphenol; 2-methyl-4-ethylphenol; 2- and 4-methoxyphenol; β-naphthol; and 8-hydroxyquinoline, with formaldehyde and dimethylamine or piperidine or morpholine.

SUMMARY OF THE INVENTION

The method of this invention for preparing the alkyl 2-[2-(secondary amino methyl)-5-alkyl phenoxy] alkanoate intermediate is safer, simpler to run, and more cost efficient than methods previously disclosed. Accordingly, this invention is a method for preparing an alkyl 2-[2-(secondary amino methyl)-5-alkylphenoxy]-alkanoate comprising the steps, in the order given: (A) reacting a first mixture of (1) m-alkyl phenol, (2) a secondary amine, and (3) formaldehyde, with or without a catalyst in a first solvent at reflux temperatures to form a 2-[(secondary amino)methyl]-5-alkylphenol; and (B) reacting a second mixture of the 2-[(secondary amino)methyl]-5-alkylphenol, (4) an alkyl 2-haloalkanoate, and (5) an alkali metal carbonate with or without a second catalyst in a second solvent at reflux temperatures to form the alkyl 2-[2-(secondary amino methyl)-5-alkylphenoxy]-alkanoate.

A further embodiment of this invention is a method of for preparing a 2-(secondary aminomethyl)-5-alkylphenol comprising reacting a mixture of (1) m-alkyl phenol, (2) a secondary amine, and (3) formaldehyde with or without a catayist in acetonitrile, at a temperature between about 25° C. and about 90° C. for about 50 minutes to 96 hours; wherein the ratio of the secondary amine (2) to the phenol (1) is about 1.0 to about 1.4 molar equivalents of the secondary amine (2) to 1 of the phenol (1); and wherein the ratio of the formaldehyde (3) to the phenol (1) is about 1.0 to about 2.2 molar equivalents of the formaldehyde (3) to 1 of the phenol (1).

Novel Mannich bases formed by the methods of this invention include a 2-[(secondary amino)methyl]-5-alkylphenol, particularly 2-(morpholin-4-ylmethyl)-5-ethylphenol; or 2-(N,N-diethylamino methyl)-5-ethylphenol and a methyl 2-[2-(secondary amino methyl)-5-alkylphenoxy]-propanoate, particularly methyl 2-[2-(morpholin-4-ylmethyl)-5-ethylphenoxy]-propanoate or 2-[2-(N,N-diethylamino methyl)-5-ethyl phenoxy] propanoate.

DETAILED DESCRIPTION OF THE INVENTION

The present invention relates to a novel use of a Mannich base, 2-[(secondary amino)methyl]-5-alkylphenol in preparing herbicidal 2-[(4-heterocyclic-substituted-3-halophenoxymethyl)-phenoxyl-alkanoates. In particular the present invention relates to a method in which a secondary amine, e.g. morpholine, is substituted into the 6-position of m-alkylphenol in the presence of paraformaldehyde or aqueous formaldehyde to form the Mannich base intermediate, for example, 2-(morpholin-4-ylmethyl)-5-alkylphenol. This reaction is highly regio-selective for the required isomer. This 2-[(secondary amino)methyl]-5-alkylphenol is then alkylated with an alkyl 2-haloalkanoate, preferably a methyl 2-halopropanoate, in the presence of a base, affording a second Mannich base intermediate, alkyl 2-[[2-(secondary amino)methyl]-5-alkylphenoxy]alkanoate, for example, methyl 2-[[2-morpholin-4-ylmethyl]-5-ethylphenoxy] propanoate. This alkylated Mannich base can then be converted to the alkyl 2-(2-halomethyl-5-alkylphenoxy) alkanoate intermediate which in turn is converted to the herbicidal 2-[(4-heterocyclic-substituted-3-halophenoxymethyl)-phenoxy]-alkanoates, for example, methyl 2-[2-[[4-[3,6-dihydro-3-methyl-2,6-dioxo4-(trifluoromethyl)-1(2H)-pyrimidinyl]phenoxy]-methyl]-5-ethylphenoxy]propanoate.

2-[(SECONDARY AMINO)METHYL]-5-ALKYLPHENOL

The method for preparing the Mannich base intermediate, 2-[(secondary amino)methyl]-5-alkylphenol, may be illustrated by the following reaction scheme:

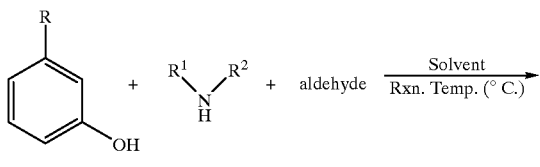

A

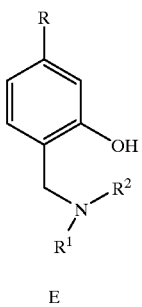

E

Referring to this scheme, the 2-8(secondary amino) methyl]-5-alkylphenol E is prepared by reacting m-alkylphenol A in a solvent, such as acetonitrile, at ambient temperature with a secondary amine, such as morpholine, at an amine to phenol A ratio of 1.0 to 1.4 molar equivalents of amine to one of phenol A, heating the mixture to 60–70° C., adding an aldehyde, such as paraformaldehyde, at an aldehyde to phenol A ratio of 1.0 to 1.4 molar equivalents of formaldehyde to one of phenol A; maintaining or heating the reaction mixture at 60° C. to reflux for one to eight hours, and recovering phenol E. The phenol E is also prepared by reacting phenol A in a solvent, such as acetonitrile, at ambient temperature or at 60° C. with a secondary amine, such as morpholine, then with an aldehyde, at an amine to phenol A ratio of 1.0 to 1.3 molar equivalents of amine to one of phenol A and at an aldehyde to phenol A ratio of 1.0 to 2.2 molar equivalents of aldehyde to one of phenol A, and maintaining the reaction mixture at ambient temperature or 60° C. for four hours to four days.

In an alternative method, phenol E is prepared by reacting phenol A with one to two molar equivalents of an aldehyde in acetonitrile, heating the mixture to 40 to 70° C., adding one to two molar equivalents of secondary amine, heating the reaction mixture at 45 to 85° C. for 50 minutes to 2.5 hours, adding additional amine in a ratio of 0.02 to 0.09 molar equivalent of amine to one of phenol A and/or additional aldehyde in a ratio of 0.02 to 0.05 molar equivalent of aldehyde to one of phenol A, maintaining the reaction mixture at 45 to 85° C. for an additional 40 minutes to one hour, and recovering phenol E.

In a preferred method (Method A) for preparing the 2-[(secondary amino)methyl]-5-alkylphenol intermediate E, 1.0 to 1.4 molar equivalents, preferably 1.2 molar equivalents, of a secondary amine, for example N,N-dimethylamine, is added to a stirred solution of a one molar equivalent of m-alkylphenol A in an alcohol, for example isopropanol. A useful concentration of the phenol A in the alcohol is in the range of 0 to 50% based on weight of phenol A per volume of alcohol. A preferred concentration of phenol A in alcohol is 50% weight/volume. Other secondary amines that have utility in the present invention include, but are not limited to, piperazine, piperidine, N,N-diethylamine, isopropylamine, pyrrolidine, N-methylpiperazine, N,N-dipropylamine, and N,N-dibutylamine. The reaction mixture is maintained at ambient temperature and 1.0 to 1.4 molar equivalents, preferably 1.2 molar equivalents, of an aldehyde, for example paraformaldehyde, is added. Upon completion of addition, the reaction mixture is either maintained at ambient temperature or heated to 60° C. and then maintained at 60° C. for four hours to four days, preferably for 17 hours, and then the product isolated in excellent yield using methods known to one skilled in the art. Example 1 provides the detailed methods by which this process is conducted.

In the most preferred method (Method B) for preparing the 2-[(secondary amino)methyl]-5-alkylphenol intermediate E, a one molar equivalent of m-alkylphenol A is added to a solvent, for example acetonitrile or toluene. A useful concentration of the phenol A in the solvent is in the range of 20 to 100% based on weight of phenol A per volume of solvent, preferably 20 to 77%, most preferably 76.3%. Upon completion of addition, the mixture is vigorously stirred at ambient temperature to effect dissolution and one to two molar equivalents, preferably 1.0 to 1.4 molar equivalents, most preferably 1.2 molar equivalents of an aldehyde, such as paraformaldehyde, is added. Upon completion of addition, the reaction mixture is stirred and then heated to 40 to 70° C., preferably 65 to 70° C., most preferably 65° C. The time that the reaction mixture is stirred is not critical, but is usually 10 to 20 minutes. Once at the prescribed temperature, a secondary amine, such as morpholine or N,N-diethylamine, is added during a one hour period at a rate to maintain the reaction temperature between 70 to 75° C. The ratio of amine used to that of phenol A is in the range of 1.0 to 2.0 molar equivalents of amine to one molar equivalent of phenol A, preferably 1.0–1.4 equivalents to one, most preferably 1.16 to 1.0. Upon completion of addition, the reaction mixture is heated to 45 to 85° C., preferably 65° C. to reflux, most preferably 70° C. The time required to reach the prescribed temperature is not critical, but is usually 10 to 20 minutes. The reaction mixture is then maintained at the prescribed temperature for about 50 minutes to 2.5 hours, preferably about one to two hours, most preferably two hours. A catalytic amount of an acid, such as hydrochloric acid, or a base, may be added to accelerate the reaction. Once the appropriate time has elapsed, the reaction mixture is analyzed by methods known to one skilled in the art to determine if the phenol starting material has been converted to the disubstituted phenol. If the phenol has been converted, the product is isolated in excellent yield using methods known to one skilled in the art. If the phenol has not been converted, an additional 0.02 to 0.09 molar equivalent of amine to one of phenol A and/or 0.02 to 0.05 molar equivalent of aldehyde to one of phenol A are added. Upon completion of addition, the reaction mixture is heated at the prescribed temperature for an additional 40 minutes to one hour, and the product isolated in excellent yield using methods known to one skilled in the art. Example 2 provides the detailed methods by which this process is conducted.

In a variation (Method C) of the most preferred method for preparing the phenol E outlined above, a solution of the phenol E and aldehyde in acetonitrile is heated to 65° C. and the secondary amine is added at a rate of 0.5 lb./min. during a two hour period. The ratios were the same as above. A useful concentration of the phenol E in the acetonitrile is 100% based on weight of phenol A per volume of acetonitrile. Upon completion of addition, the reaction mixture is heated to 65–75° C. where it is maintained for three hours. After this time, the product is isolated in excellent yield using methods known to one skilled in the art. Example 3 provides the detailed methods by which this process is conducted.

ALKYL 2-[2-(SECONDARY AMINO)METHYL-5-ALKYLPHENOXY]-ALKANOATE

The method for preparing the Mannich base intermediate, alkyl 2-[2-(secondary amino methyl)-5-alkylphenoxy] alkanoate, may be illustrated by the following reaction scheme in which one alkyl group is methyl and the alkanoate group is propanoate:

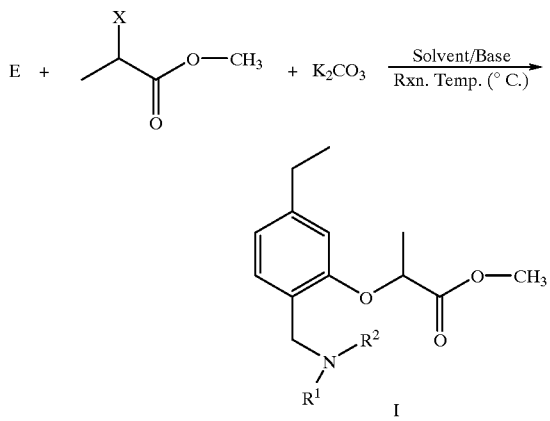

where X = Br or Cl

Referring to this scheme, the 2-[(secondary amino) methyl]-5-alkylphenol E is taken up in a solvent, such as toluene, DMF, methylethylketone, or acetonitrile, and then reacted with a alkyl 2-haloalkanoate, such as methyl 2-bromopropanoate, at a propanoate to phenol E ratio of 1.1 to 1.3 molar equivalents of alkanoate to one of phenol E, followed by potassium carbonate, at a carbonate to phenol E ratio of 1.1 to 1.3 molar equivalents of carbonate to one of phenol E; heating the reaction mixture to reflux, maintaining the mixture at reflux for six to 28 hours, adding an additional 0.05 molar equivalents of the alkyl 2-haloalkanoate if necessary, and maintaining the reaction mixture for an additional hour, recovering the alkyl 2-[[2-(secondary amino)methyl]-5-ethylphenoxy]alkanoate I.

In the alkyl 2-haloalkanoate used in the method of this invention, the alkyl group is a methyl group, an ethyl group or a propyl group; the alkanoate group is a methanoate group, an ethanoate group or a propanoate group; and the halo group is a chloro group, a bromo group or an iodo group. Preferably the alkyl 2-haloalkanoate is methyl 2-bromopropanoate or methyl 2-chloropropanoate. In the following description, methyl 2-bromopropanoate is used as the alkyl 2-haloalkanoate to illustrate the method of this invention but is not intended to be limited thereby.

In an alternative method, alkyl 2-[[2-(secondary amino) methyl]-5-alkylphenoxy]propanoate I is prepared by reacting the intermediate E with one to three molar equivalents of base in a solvent such as N,N-dimethylformamide or with one to four molar equivalents of a base, such as triethylamine, in a solvent such as acetonitrile, heating the reaction mixture to 45 to 150° C., adding one to three molar equivalents of a alkyl 2-halopropanoate, such as methyl 2-bromopropanoate, maintaining the reaction mixture at 45 to 150° C. for 30 minutes to about 28 hours, and either recovering propanoate I, or adding an additional 0.05 to 1.2 molar equivalents of the alkyl 2-halopropanoate, carbonate, and/or base, maintaining the reaction mixture at 75 to 130° C. for an 40 minutes to about 18 hours, and then recovering alkyl 2-[[2-(secondary amino)methyl]-5-alkylphenoxy] propanoate I.

In a preferred method (Method D) for preparing the alkyl 2-[2-(secondary amino methyl)-5-alkylphenoxy]propanoate intermediate I, a solution of a one molar equivalent of the phenol intermediate E in a solvent, such as acetonitrile, a tertiary amine, for example triethylamine, and potassium carbonate are added to a round bottom flask. The reaction mixture is then heated to 45–150° C., preferably 70° C. The ratio of tertiary amine to phenol E is in the range of one to four molar equivalents of amine to one molar equivalent of phenol E, preferably one to three to one. The ratio of potassium carbonate used to that of phenol E is one to three molar equivalents of potassium carbonate to one molar equivalent of phenol E, preferably 1.0–2.5 to one. A useful concentration of the phenol E in the solvent is in the range of 0 to 50% based on weight of phenol E per volume of solvent, preferably 5 to 30%. In addition to potassium carbonate other bases that have utility in the present invention include, but are not limited to, potassium hydroxide, sodium hydroxide, potassium ethoxide, potassium 4-butoxide, and calcium hydroxide. Once at the prescribed temperature, an alkyl 2-halopropanoate, such as methyl 2-bromopropanoate, is added at a ratio of one to three molar equivalents of propanoate to one molar equivalent of phenol E, preferably 1.0–2.5 to one. A catalytic amount of a phase transfer catalyst, including, but not limited to, tetra-n-butyl ammonium bromide, methyl tri-n-butyl ammonium hyrdoxide (40% aq), methyl trioctyl ammonium bromide, dodecyl trimethyl ammonium bromide, methyl triethyl ammonium chloride, tricaprylyl methyl ammonium chloride, tris[2-2(2-methoxyethoxy)ethyl]amine, dodecyl ethyl dimethyl ammonium bromide, tetraethylammonium chloride monohydrate, tetrabutylammonium hydrogen sulfate, and tetrabutylammonium sulfate (50% aq) may be added at this time to promote decomposition. Upon completion of addition, the reaction mixture is heated to 45–15° C., preferably 75–80° C., most preferably at reflux, where it is maintained for 30 minutes to about 28 hours, preferably 1.0 to 12 hours. Once the appropriate time has elapsed, the reaction mixture is analyzed by methods know to one skilled in the art to determine if the phenol starting material has been converted to the propanoate I. If the phenol has been converted, the product is isolated in excellent yield using methods known to one skilled in the art. If the phenol has not been converted, an additional 0.05 to 1.2 molar equivalents of the alkyl 2-halopropanoate, carbonate, and/or base to one of phenol A are added. Upon completion of addition, the reaction mixture is heated at the prescribed temperature for an additional 40 minutes to 18 hours, and the product isolated in excellent yield using methods known to one skilled in the art. Other solvents that have utility in the present invention are, but are not limited to, N,N,-dimethylacetamide, N,N-dimethylformamide, toluene, and methyl 2-chloropropanoate. Example 4 provides the detailed methods by which this process is conducted.

In the most preferred method (Method F) for preparing the alkyl 2-[2-(secondary methyl)-5-alkylphenoxy] propanoate intermediate I, potassium carbonate, one molar equivalent of the phenol intermediate E, and N,N-dimethylformamide are added to a round bottom flask. The reaction mixture is then heated to 40–110° C., preferably 70–110° C. The ratio of potassium carbonate used to that of phenol E is one to three molar equivalents of potassium carbonate to one molar equivalent of phenol E, preferably one to two to one. A useful concentration of the phenol E in the N,N-dimethylformamide is in the range of 5 to 200% based on weight of phenol E per volume of solvent, preferably 10 to 150%. Once at the prescribed temperature, an alkyl 2-halopropanoate, such as methyl 2-chloropropanoate, is added at a ratio of one to three molar equivalents of propanoate to one molar equivalent of phenol E, preferably one to two to one. Upon completion of addition, the reaction mixture is heated to 100–140° C., preferably 100–130° C., where it is maintained for 45 minutes to about 8 hours, preferably three to seven hours. Once the appropriate time has elapsed, the reaction mixture is analyzed by methods know to one skilled in the art to determine if the phenol starting material has been converted to the propanoate I. If the phenol has been converted, the product is isolated in excellent yield using methods known to one skilled in the art. If the phenol has not been converted, an additional 0.05 to 1.2 molar equivalents of the alkyl 2-halopropanoate and/or carbonate to one of phenol A are added. Upon completion of addition, the reaction mixture is heated at the prescribed temperature for an additional 90 minutes to 212 minutes, and the product isolated in excellent yield using methods known to one skilled in the art. This reaction runs just as efficiently in a closed system as it does in an open system. Example 6 provides the detailed methods by which this process is conducted.

In a variation (Method E) of the preferred method for preparing the propanoate I outlined above, a solution of the phenol E, tertiary amine, and potassium carbonate in acetonitrile is heated to 70° C. and the methyl 2bromopropanoate is added during a two hour period at a rate to maintain the reaction temperature at 65–7° C. The ratios were the same as above. A useful concentration of the phenol E in the acetonitrile is 14.1% based on weight of phenol E per volume of acetonitrile. Upon completion of addition, the reaction mixture is maintained at 65–70° C. for seven hours. Once the -appropriate time has elapsed, the reaction mixture is analyzed by methods know to one skilled in the art to determine if the phenol starting material has been converted to the propanoate. If the phenol has been converted, the product is isolated in excellent yield using methods known to one skilled in the art. If the phenol has not been converted, an additional 0.12 molar equivalent of amine to one molar equivalent of phenol, 0.17 molar equivalent of carbonate to one molar equivalent of phenol, and 0.16 molar equivalent of propanoate to one molar equivalent of phenol are added. Upon completion of addition, the reaction mixture is heated at 65–70° C. for an additional hour, and the product isolated in excellent yield using methods known to one skilled in the art. Example 6 provides the detailed methods by which this process is conducted.

In an alternate method (Method G) for preparing the propanoate I, a solution of the phenol intermediate E, alkyl 2-halopropanoate, and potassium carbonate in methylethylketone is heated to reflux where it is maintained for 27 hours. After this time, the product is isolated in excellent yield using methods known to one skilled in the art. The ratios of the alkyl 2-halopropanoate to phenol and potassium carbonate to phenol are both 1.2 molar equivalents of propanoate or carbonate to one molar equivalent of phenol. A useful concentration of the phenol E to methylethylketone is 10% based on weight of phenol E per volume of methylethylketone. Example 7 provides the detailed methods by which this process is conducted. The propanoate I can then be reacted with methylchloroformate in the presence of toluene in the manner known in the art as disclosed by Yankep and Charles [Tetrahedron Lett. 28 (4), 427–430 (1987)], the disclosure of which is incorporated herein by reference, to form the alkyl 2-(2-chloromethyl-5-ethylphenoxy)-propanoate.

The intermediate alkyl 2-(2-chloromethyl-5-alkylphenoxy)propanoate K is then converted into the herbicidal 2-[(4-heterocyclic-substituted-3-halophenoxymethyl)-phenoxy]-alkanoates in the manner disclosed in U.S. Pat. No. 5,344,812, the disclosure of which is incorporated herein by reference.

The process of the present invention for preparing the 2-[(secondary amino)methyl]-5-alkyl and alkyl 2-[2-(secondary amino)methyl-5-alkyl phenoxy]alkanote intermediates can be used in preparing these herbicidal alkanotes and as such serves as an alternative method to that disclosed in U.S. Pat. No. 5,344,812. In contrast to the patented process, the process of the present invention is safer, simpler to run, and more cost efficient. In the process of the present invention, an amine is selectively added to a phenol and then this phenol is selectively alkylated to generate the propanoate intermediate which in turn can be converted to the herbicidal 2-[(4-heterocyclic-substituted-3-halophenoxymethyl)-phenoxy]-alkanoates. Therefore, the present process is inherently much simpler than the disclosed process in the patent. In addition, the present process places a secondary amine in the 6-position of m-ethylphenol providing high yields of the 2-[(secondary amino)methyl]-5-ethylphenol intermediate. The regio-selective substitution and high yields of the 2-[(secondary amino)methyl]-5-ethylphenol isomer were unexpected because of the steric hindrance offered by the ethyl group in the 3-position. In addition, the process of the present invention may be conducted in one reaction vessel, not in two as taught in U.S. Pat. No. 5,344,812. This procedure eliminates the waste associated with the transfer of reaction mixtures from one vessel to another. This procedure also eliminates the use of methylene chloride which is an environmentally unfriendly solvent.

The preparation methods of this invention will now be illustrated by the following examples but is not intended to be limited thereby.

EXAMPLE 1

Method A—Preparation of 2-[(N,N-dimethylamino) methyl]-5-ethylphenol Using Isopropanol as the Solvent and N,N-dimethylamine as the Secondary Amine To a 25 mL round bottom flask equipped with a mechanical stirrer and a thermometer was added 4 mL (%Wt/Vol. Phenol to Solvent—50%) of isopropanol, followed by 2.0 grams (0.0164 mole—1.0 equiv.) of m-ethylphenol and then 2.22 grams (0.0197 mole—1.2 equiv.) of an aqueous 40% N,N-dimethylamine solution. The mixture was stirred at ambient temperature to effect dissolution, and 0.59 gram (0.0197 mole—1.2 equiv.) of paraformaldehyde was added. The reaction mixture began to exotherm so it was cooled to ambient temperature where it stirred for 17 hours. After this time, the reaction mixture was concentrated under reduced pressure to a residue, and the residue was taken up in heptane and water. The organic layer was separated, washed with an aqueous saturated sodium chloride solution, dried with magnesium sulfate, and filtered. The filtrate was concentrated under reduced pressure, yielding 2.8 grams of 2-[(N,N-dimethylamino)methyl]-5-ethylphenol (88.7% yield). Gas Chromatography (GC) analysis of the product indicated the presence of about 7% of an impurity. The NMR spectrum was consistent with the proposed structure.

EXAMPLE 2

Method B—Preparation of 2-(Morpholin-4-ylmethyl)-5-ethylphenol Using Acetonitrile as the Solvent and Morpholine as the Secondary Amine To a stirred solution of 244.0 grams (1.78 moles—1.0 equiv.) of 89.1% pure m-ethylphenol in 320 mL (%Wt/Vol.

Phenol to Solvent—76.3%) of acetonitrile was added 67.6 grams (2.14 moles—1.2 equiv.) of paraformaldehyde. Upon completion of addition, the mixture was stirred for ten minutes and then heated to 65° C. where 179.5 grams (2.06 moles—1.16 equiv.) of morpholine was added during a one hour period at a rate to maintain the reaction temperature below 70–75° C. Upon completion of addition, the reaction mixture was heated to 70° C. where it stirred for two hours. At this point, the reaction mixture was analyzed by GC, which indicated that 2% of the phenol starting material remained. An additional 3.5 grams (0.04 mole—0.02 equiv.) of morpholine was added. Upon completion addition, the reaction mixture was stirred at 70° C. until GC analysis indicated that 1.1% of the phenol starting material remained. The acetonitrile was removed under vacuum, yielding 446.6 grams of 89.1% pure 2-(morpholin-4-ylmethyl)-5-ethylphenol (90% yield).

EXAMPLE 3

Method C—Preparation of 2-(Morpholin-4-ylmethyl)-5-ethylphenol Using Acetonitrile as the Solvent and Morpholine as the Secondary Amine To a 50 gallon glass lined reactor was added 23.07 pounds (0.769 mole—1.04 equiv.) of paraformaldehyde, followed by 92 pounds (%Wt/Wt Phenol to Solvent—100%) of acetonitrile, and then 92 pounds (0.739 mole—1.0 equiv.) of 98.0% pure m-ethylphenol. The mixture was heated to 65° C., and 66.2 pounds (0.761 mole—1.03 equiv.) of morpholine was added at a rate of 0.5 lb./min. during a two hour period. Upon completion of addition, the reaction mixture was heated to 65–70° C. where it stirred for three hours. After this time, the reaction mixture was concentrated under vacuum at 70° C., yielding 171 pounds of 89.4% pure 2-(morpholin4-ylmethyl)-5-ethylphenol (93% yield).

EXAMPLE 4

Method D—Preparation of Methyl 2-[2-(morpholin4-ylmethyl)-5-ethylphenoxy]propanoate using Acetonitrile as a Solvent and Methyl 2-bromopropanoate as the Alkylating Agent To a 5 liter round bottom flask equipped with a mechanical stirrer and a thermometer was added 331.5 grams (1.34 moles—1.0 equiv.) of 89.1% pure 2-(morpholin-4-ylmethyl)-5-ethylphenol, followed by 3000 mL (%Wt/Vol. Phenol to Solvent—11.1%) of acetonitrile, 166.98 grams (1.65 moles—1.23 equiv.) of triethylamine and 310.5 grams (2.25 moles—1.68 equiv.) of potassium carbonate. The mixture was heated to 78° C., and 350.7 grams (2.1 moles—1.57 equiv.) of methyl 2-bromopropanoate was added during a ten minute period. Upon completion of addition, the reaction mixture was analyzed by GC which indicated the reaction was incomplete. The reaction mixture was heated to reflux where it stirred for four hours. After this time, the reaction mixture was again analyzed by GC, which indicated 6.8% of the starting material remained. The reaction mixture was stirred at reflux for an additional hour and then analyzed a third time by GC, which indicated that 3.5% of the starting material remained. The reaction mixture was stirred for an additional five hours and then analyzed by a fourth time by GC, which indicated that the reaction was complete. The reaction mixture was filtered, and the filtrate was concentrated under reduced pressure, yielding 510.0 grams of material. The material was taken up in 1000 mL of toluene, and the resulting solution was washed with two 750 mL portions of a 2.5% aqueous sodium carbonate solution. The organic layer was separated and concentrated under reduced pressure to an oil. The above dissolution, washing, and concentration was repeated, yielding 439.4 grams of 84.8% pure methyl 2-[2-(morpholin-4-ylmethyl)-5-ethylphenoxy]propanoate (94.6% yield).

EXAMPLE 5

Method E—Preparation of Methyl 2-[2-(morpholin-4-ylmethyl)-5-ethylphenoxy]propanoate using Acetonitrile as a Solvent and Methyl 2-bromopropanoate as the Alkylating Agent To a 200 gallon reactor was added 582 pounds (%Wt/Wt Phenol to Solvent—14.1%) of acetonitrile, followed by 82 pounds (0. 323 mole—1.0 equiv.) of 87% pure 2-(morpholin-4-ylmethyl)-5-ethylphenol, 72.4 pounds (0.717 mole—2.22 equiv.) of triethylamine, and 99.0 pounds (0.717 mole—2.22 equiv.) of potassium carbonate. The mixture was heated to 70° C., and 90.1 pounds (0.539 mole—1.67 equiv.) of methyl 2-bromopropanoate was added during a two hour period a rate to maintain the reaction temperature at 65–70° C. Upon completion of addition, the reaction mixture was stirred at to 65–70° C. for seven hours. After this time, the reaction mixture was analyzed by GC, which indicated that 8% of the phenol starting material remained. An additional 9.0 pounds (0.054 mole—0.16 equiv.) of methyl 2-bromopropanoate, 8.0 pounds (0.058 mole—0.17 equiv.) of potassium carbonate, and 4.0 pounds (0.040 mole—0.12 equiv.) of triethylamine were added. Upon completion of addition, the reaction mixture is stirred at 65–70° C. for an additional hour. At the conclusion of this period, the reaction mixture is filtered, and the filtrate was concentrated under vacuum at 70° C. to yield an oil. The oil was taken up in 213 pounds of toluene and 185 pounds of a 2.5% aqueous sodium carbonate solution. The organic layer is separated from the aqueous layer and concentrated under vacuum at 90° C., yielding 106.0 pounds of 86.2% pure methyl 2-[2-(morpholin-4-ylmethyl)-5-ethylphenoxy]propanoate (92% yield).

EXAMPLE 6

Method F—Preparation of Methyl 2-[2-(morpholin-4-ylmethyl)-5-ethylphenoxy]propanoate using N,N-Dimethylformamide as a Solvent and Methyl 2-chloropropanoate as the Alkylating Agent To a one liter round bottom flask equipped with a mechanical stirrer and a thermometer was added 157.13 grams (1.14 moles—1.3 equiv.) of potassium carbonate, followed by 215.27 grams (0.875 mole—1.0 equiv.) of 89.9% pure 2-(morpholin-4-ylmethyl)-5-ethylphenol, and 230 mL (%Wt/Vol. Phenol to Solvent—93.6%) of N,N-dimethylformamide. The mixture was vigorously stirred and heated to 110° C., and then 139.3 grams (1.14 moles—1.3 equiv.) of methyl 2-chloropropanoate was added during a one hour period. Upon completion of addition, the reaction mixture was analyzed by GC, which indicated the reaction was incomplete. The reaction mixture was heated at 110° C. for seven hours. After this time, the reaction mixture was again analyzed by GC, which indicated the reaction was complete. The reaction mixture was filtered, and the orange filtrate was kept under a nitrogen atmosphere for about 48 hours. After this time, the filtrate was concentrated under vacuum at 90° C. and 10 mm of mercury to yield a red, brown liquid. The liquid was taken up in 200 mL of toluene, and the resulting solution was washed with two 500 mL portions of an aqueous saturated sodium chloride solution.

The organic layer was separated from the aqueous layer, dried with magnesium sulfate, and filtered. The filtrate was concentrated under vacuum at 90° C. and 10 mm of mercury, yielding 252.7 grams of 83.6% pure methyl 2-[2-(morpholin-4-ylmethyl)-5-ethylphenoxy]propanoate (78.6% yield). The NMR spectrum was consistent with the proposed structure.

EXAMPLE 7

Method G—Preparation of Methyl 2-[2-(morpholin-4-ylmethyl)-5-ethylphenoxy]propanoate using Methylethylketone as a Solvent and Methyl 2-bromopropanoate as the Alkylating Agent To a 250 mL round bottom flask equipped with a mechanical stirrer and a thermometer was added 5.0 grams (0.0.023 mole—1.0 equiv.) of 2-(morpholin-4-ylmethyl)-5-ethylphenol, 4.54 grams (0.027 mole—1.2 equiv.) of methyl 2-bromopropanoate, 3.75 grams (0.027 mole—1.2 equiv.) of potassium carbonate, and 50 mL (%Wt/Vol. Phenol to Solvent—10%) of methylethylketone. The reaction mixture was heated to reflux where it stirred for 27 hours. After this period, the reaction mixture was analyzed by GC, which indicated the reaction was complete. The reaction mixture was filtered and washed with diethylether. The filtrate was concentrated under reduced pressure, yielding 7.0 grams of 96% pure methyl 2-[2-(morpholin4-ylmethyl)-5-ethylphenoxy]propanoate (95.2% yield).

EXAMPLE 8

Method D—Preparation of Methyl 2-[2-(morpholin-4-ylmethyl)-5-ethylphenoxy]propanoate using Acetonitrile as a Solvent and Methyl 2-bromopropanoate as the Alkylating Agent This compound was prepared in the manner of Example 4, using 221.0 grams (0.92 mole—1.0 equiv.) of 92.0% pure 2-(morpholin-4-ylmethyl)-5-ethylphenol, 202.3 grams (2.17 moles—2.36 equiv.) of triethylamine, 276.0 grams (2.17 moles—1.68 equiv.) of potassium carbonate, and 250.0 grams (1.63 moles—1.77 equiv.) of methyl 2-bromopropanoate in about 2000 mL (%Wt/Vol. Phenol to Solvent—11.1 %) of acetonitrile. This preparation differs in that the mixture was heated to 70° C. rather than 78° C. before the methyl 2-bromopropanoate was added and that the methyl 2-bromopropanoate was added during a 15 minute period at a rate to maintain the reaction temperature between 70–75° C. rather than during a ten minute period. A yield of 311 grams of 85.3% pure methyl 2-[2-(morpholin-4-ylmethyl)-5-ethylphenoxy]-propanoate was obtained (93.9% yield).

What is claimed:

1. A method for preparing an alkyl 2-[2-(secondary amino methyl)-5-alkylphenoxy]-alkanoate comprising the steps in the order given:
    (A) reacting a first mixture of (1) m-alkyl phenol, (2) a secondary amine, and (3) an aldehyde with or without a catalyst in a first solvent at reflux temperatures to form a 2-[(secondary amino)methyl]-5-alkylphenol; and
    (B) reacting a second mixture of the 2-[(secondary amino) methyl]-5-alkylphenol, (4) an alkyl 2-haloalkanoate, and (5) an alkali metal carbonate with or without a second catalyst in a second solvent at reflux temperatures to form the alkyl 2-[2-(secondary amino methyl)-5-alkylphenoxy]-alkanoate.

2. The method of claim 1 wherein the secondary amine is selected from the group consisting of N,N-dimethylamine, N,N-diethylamine, N,N-dipropyl-amine, N,N-dibutylamine, morpholine, piperazine, piperidine, and pyrrolidine.

3. The method of claim 1 wherein the aldehyde is selected from the group consisting of paraformaldehyde, aqueous formaldehyde, formaldehyde, and polymerized acetal derivatives.

4. The method of claim 1 wherein the first solvent is acetonitrile or toluene.

5. The method of claim 1 wherein the alkyl group of the alkyl 2-haloalkanoate is a methyl group, an ethyl group, or a propyl group.

6. The method of claim 1 wherein the alkanoate group of the alkyl 2-haloalkanoate is a methanoate group, an ethanoate group, or a propanoate group.

7. The method of claim 1 wherein the alkyl 2-haloalkanoate is methyl 2-bromopropanoate or methyl 2-chloropropanoate.

8. The method of claim 1 wherein the alkali metal carbonate is potassium carbonate or sodium methoxide.

9. The method of claim 1 wherein the second solvent is selected from the group consisting of acetonitrile, toluene, N,N-dimethylformamide, and methylethylketone.

10. The method of claim 1 wherein the second catalyst is selected from the group consisting of tetra-n-butyl ammonium bromide, methyl tri-n-butyl ammonium hyrdoxide (40% aq), methyl trioctyl ammonium bromide, dodecyl trimethyl ammonium bromide, methyl triethyl ammonium chloride, tricaprylyl methyl ammonium chloride, tris[2-2(2-methoxyethoxy)ethyl]amine, dodecyl ethyl dimethyl ammonium bromide, tetraethylammonium chloride monohydrate, tetrabutylammonium hydrogen sulfate, and tetrabutylammonium sulfate (50% aq).

11. The method of claim 1 wherein the first mixture is refluxed for about 50 minutes to about 96 hours.

12. The method of claim 1 wherein the ratio of the amine (2) to the phenol (1) is about 1.0 to about 1.4 molar equivalents of the amine (2) to 1 of the phenol (1), and the ratio of the aldehyde (3) to the phenol (1) is about 1.0 to about 2.2 molar equivalents of the aldehyde (3) to 1 of the phenol (1).

13. The method of claim 1 wherein the second mixture is reacted at a temperature between about 45° C. and about 150° C. for about 30 minutes to about 28 hours.

14. The method of claim 1 wherein the ratio of the alkyl 2-haloalkanoate (4) to the a 2-[(secondary amino)methyl]-5-alkylphenol is about 1.1 to about 1.3 molar equivalents of the alkyl 2-haloalkanoate (4) to 1 of the a 2-[(secondary amino)methyl]-5-alkylphenol.

15. The method of claim 1 wherein the ratio of the base (5) to the 2-[(secondary amino)methyl]-5-alkylphenol is about 1.1 to about 1.3 molar equivalents of the base (5) to 1 of the 2-[(secondary amino)methyl]-5-alkylphenol.

* * * * *